(12) United States Patent
Furuichi et al.

(10) Patent No.: US 7,507,563 B2
(45) Date of Patent: Mar. 24, 2009

(54) PROCESS FOR PRODUCING 1, 4-DIHYDROXY-2-NAPHTHOIC ACID

(75) Inventors: Keisuke Furuichi, Odawara (JP); Nobuo Yoda, Tokyo (JP)

(73) Assignee: Meiji Dairies Corporation, Tokyo (JP)

( * ) Notice: Subject to any disclaimer, the term of this patent is extended or adjusted under 35 U.S.C. 154(b) by 282 days.

(21) Appl. No.: 10/574,283

(22) PCT Filed: Sep. 30, 2004

(86) PCT No.: PCT/JP2004/014394

§ 371 (c)(1),
(2), (4) Date: Mar. 31, 2006

(87) PCT Pub. No.: WO2005/033323

PCT Pub. Date: Apr. 14, 2005

(65) Prior Publication Data

US 2007/0066685 A1    Mar. 22, 2007

(30) Foreign Application Priority Data

Oct. 1, 2003    (JP)    ............................. 2003-343211

(51) Int. Cl.
*C12P 7/42*    (2006.01)
(52) U.S. Cl. ..................................... 435/146
(58) Field of Classification Search ........................ None
See application file for complete search history.

(56) References Cited

U.S. PATENT DOCUMENTS 7,374,915 B2 *   5/2008   Sato et al. .................... 435/136
2004/0241815 A1   12/2004  Sato et al.

FOREIGN PATENT DOCUMENTS

ES    2102332    7/1997
JP    2002/540760    12/2002
WO    03/016544    2/2003
WO    2004/085364    10/2004

OTHER PUBLICATIONS

U.S. Appl. No. 10/574,283, filed Mar. 31, 2006, Furuichi et al.
Isawa, Kakuhei et al., "Isolation and Identification of a New Bifidogenic Growth Stimulator Produced by Propionibacterium freudenreichii ET-3, Biosci. Biotechnol. Biochem.", vol. 66, No. 3, pp. 679-681, 2002.
Ye, Kaiming et al., "Efficient Production of Vitamin B12 from Propionic Acid Bacteria under Periodic Variation of Dissolved Oxygen Concentration", Journal of Fermentation and Bioengineering, vol. 82, No. 5, pp. 484-491, 1996.
Miyano, Kenichiro et al., "Production of Vitamin B12 by propionic acid bacteria in a filtering-culture system and in a periodically-controlled culturing sysytem", The Society of Chemical Engineers, vol. 30th, p. 316, 1997. (with English translation).
Ishida, Junya et al., "Production of Bifidobacteria-specific growth stimulator by Propionic acid bacteria in anaerobic culture systems", Japan Society for Bioscience, p. 8, 2002. (with English translation).
Okada, Yoshikiyo et al., "Study on the anti-inflammatory action of DHNA against DSS enteritis, a component of the whey fermentation substance produced by the Propionic acid bacterium", Digestive organ and immunology, No. 40, pp. 58-60, 2003. (with partial English translation).
Hojo, Kenichi et al., "Bifidogenic Growth Stimulator Produced by Propionic Acid Bacteria", The Diary Science symposium 2000, vol. 49, No. 3, pp. 161-167, 2000. (with partial English translation).

* cited by examiner

*Primary Examiner*—Herbert J. Lilling
(74) *Attorney, Agent, or Firm*—Oblon, Spivak, McClelland, Maier & Neustadt, P.C

(57) ABSTRACT

A process for producing 1,4-dihydroxy-2-naphtoic acid, comprising initiating the culture of 1,4-dihydroxy-2-naphthoic acid producing bacteria belonging to propionic acid bacteria under anaerobic conditions and culturing the bacteria under aeration into a medium when the concentration of a carbon source in the medium is 3.5% by mass or less.

12 Claims, 3 Drawing Sheets

Time-dependent changes in concentration of DHNA

Time-dependent changes in concentration of lactose

Time-dependent changes in number of propionic acid bacteria

Time-dependent changes in concentration of propionic acid

Time-dependent changes in concentration of acetic acid

Time-dependent changes in concentration of DHNA

PROCESS FOR PRODUCING 1,4-DIHYDROXY-2-NAPHTHOIC ACID

TECHNICAL FIELD

The present invention relates to a process for producing a high concentration of 1,4-dihydroxy-2-naphthoic acid (hereinafter it may be referred to as DHNA) using a propionic acid-bacterial fermentation and a technique for improving flavor of the culture thereof.

BACKGROUND ART

DHNA has been known to be useful for industrial materials as dyes, pigments or photographic sensitive materials, and heretofore various synthetic methods by organic chemical synthesis have been developed. As a result of extensive studies by the inventors of the present invention on alternative method for production of DHNA, they have found that a large amount of DHNA could be produced by propionic acid bacteria in or outside the cell and they have found that a composition containing DHNA, or 1,4-dihydroxy-2-naphthoic acid or a salt thereof isolated from the culture had an action for reducing abdominal discomfort caused by lactose intolerance observed at the time of ingestion of milk and at the same time it was useful for prevention and treatment of metabolic bone disease (Patent document 1).

Although according to such a method, it has become possible to use DHNA for beverages and pharmaceutical products, the composition containing DHNA is not always satisfactory in terms of flavor and as a result it has been difficult to use it frequently for commercial products. [Patent document 1]: WO 03/016544

DISCLOSURE OF THE INVENTION

Problem to be Solved by the Invention

An object of the present invention is to provide an effective process for production of a composition containing DHNA, which is improved in flavor, by the propionic acid fermentation.

Means for Solving the Problem

The present inventors have obtained unexpectedly, as a result of extensive studies from the standpoint of various fields in order to obtain composition containing DHNA with suppressed bitter taste, useful novel knowledge indicating that the concentration of DHNA in the culture was increased by aeration in the medium at a specific period during the propionic acid fermentation. The inventors have also found that the concentration of DHNA was increased by adding nutrient carbon sources of propionic acid bacteria in the culture after the cultivation and let it stand at low-temperature under weak alkaline conditions, even after culturing was terminated. In addition, the inventors have found that bitterness of thus obtained composition containing DHNA was suppressed and thus the flavor was improved; and for this, it was found useful for food, beverages or pharmaceutical products.

The present invention provides a process for producing 1,4-dihydroxy-2-naphtoic acid comprising culturing the 1,4-dihydroxy-2-naphthoic acid producing bacteria belonging to propionic acid bacteria first under anaerobic conditions and initiating aeration in a medium when the concentration of a carbon source in the medium is 3.5% or less by mass.

The present invention also provides a process for producing 1,4-dihydroxy-2-naphtoic acid comprising culturing 1,4-dihydroxy-2-naphthoic acid producing bacteria belonging to propionic acid bacteria under anaerobic conditions, adding a carbon source to the obtained culture and preserving the culture at 3 to 20° C. under weak alkaline conditions.

The present invention further provides a process for producing 1,4-dihydroxy-2-naphtoic acid comprising initiating the culture of 1,4-dihydroxy-2-naphthoic acid producing bacteria belonging to propionic acid bacteria under anaerobic conditions, culturing the bacteria with aeration in a medium when the concentration of a carbon source in the medium is 3.5% by mass or less, adding the carbon source to the obtained culture and preserving the culture at 3 to 20° C. under weak alkaline conditions.

The present invention further provides a composition containing 1,4-dihydroxy-2-naphthoic acid obtained as described hereinabove.

The present invention further provides food and beverages for improving abdominal discomfort, an agent for improving abdominal discomfort, food and beverages for preventing and treating metabolic osteopathy, or an agent for preventing and treating metabolic osteopathy, comprising the composition containing 1,4-dihydroxy-2-naphthoic acid as an active ingredient obtained as described hereinabove.

The present invention further provides use of the composition containing 1,4-dihydroxy-2-naphthoic acid obtained as described hereinabove for producing food and beverages for improving abdominal discomfort, an agent for improving abdominal discomfort, food and beverages for preventing and treating metabolic osteopathy or an agent for preventing and treating metabolic osteopathy.

The present invention further provides a method for treating abdominal discomfort or a method for treating metabolic osteopathy comprising administering an effective amount of the composition containing 1,4-dihydroxy-2-naphthoic acid obtained as described hereinabove.

Advantage of the Invention

According to the present invention, DHNA can be produced efficiently and a composition containing the obtained DHNA has a good flavor and is useful for food, beverages and pharmaceuticals.

BEST MODE FOR CARRYING OUT THE INVENTION

Figure 1:
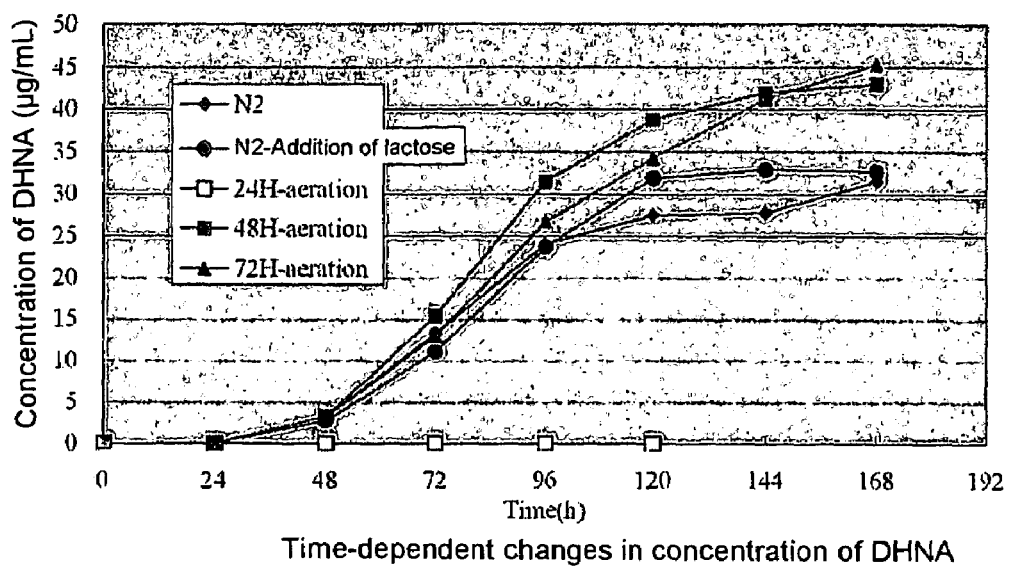
FIG. 1 shows changes in concentration of DHNA due to varied initiation times of aeration.

Examples of propionic acid bacteria used for the process for production of the present invention are not specifically limited as long as it is DHNA producing bacteria, and are microorganisms belonging to genus *Propionibacterium*, for example bacteria for production of cheese such as *Propionibacterium freudenreichii*, *Propionibacterium thoenii*, *Propionibacterium acidipropionici* and *Propionibacterium jensenii*, and *Propionibacterium avidum*, *Propionibacterium acnes*, *Propionibacterium lymphophilum* and *Propionibacterium granulosam*. Among them, *Propionibacterium freudenreichii* is preferable and *P. freudenreichii* IFO 12424, *P. freudenreichii* ATCC 6207 and *P. freudenreichii* ET-3 (FERM P-18454) are particularly preferable.

Medium used for the method of the present invention is preferably a medium containing carbon source. The carbon source used in the present invention means assimilable carbon source for propionic acid bacteria. For example, lactose, glucose, lactic acid, glycerol, gluten, cellulose, etc. can be mentioned, and lactose is especially preferable. Amount of carbon source content in the medium before initiation of the culture is 4 to 8% by mass, preferably 4 to 7% by mass, more preferably 4 to 6.7% by mass. Among them, examples of the medium, which contains lactose as the carbon source, are whey powder, casein, skim milk, or whey protein concentrate, which is a product having a reduced lactose content obtainable by dialyzing the whey, or a whey protein-separate, which is a highly purified product with highly separated lactose content. These substances can be used without modification, or they can be used with protease treatment, and the medium can be prepared by adding yeast extract, peptone such as tripticase, proper quantity of saccharides, for example, monosaccharide and/or disaccharide, which can be assimilable carbon source for propionic acid bacteria, such as glucose, lactose or lactose treated with lactase, lactic acid, glycerol, gluten, cellulose, mineral such as whey mineral, and if required, animal and plant foodstuff containing rich minerals such as oyster and ginger, or extract thereof. An embodiment of a method for preparing a medium having as a main component of its raw material a protease-treated skim milk is shown hereinbelow.

Skim milk is dissolved in water to result in 10 to 20% by mass and temperature was adjusted at 47° C. Protease corresponding to 2.5% by mass of the amount of skim milk was added thereto for hydrolysis of protein in the skim milk solution. Examples of protease are proteolytic enzyme derived from animal and plant origin or bacteria origin, and any of acidic, neutral or alkaline protease can be used. Hydrolysis is performed for 6 hours, and temperature during the hydrolysis is maintained at 47° C. and pH is adjusted to 6.8. For adjusting pH, aqueous solution of potassium carbonate is used. When the hydrolysis with protease is finished, the skim milk solution is heated to 80° C. and maintained for 10 minutes to inactivate the protease. After the inactivation, water is added so that the concentration of the skim milk becomes 10% by mass, and brewer's yeast weighing 1 to 10% by mass of the skim milk, preferably 3 to 7% by mass, is added and then sterilized. Sterilizing condition is at 121° C. for 7 minutes or more in case of using autoclave, and 140° C. or more for 4 seconds or more in case of using plate for sterilization. The thus obtained medium contains generally 4 to 5% by mass of lactose.

Culture is performed under anaerobic conditions. The anaerobic condition can be performed by using nitrogen gas, helium gas, argon gas, hydrogen gas and other inert gas, alone or in combination with one or two or more, and among them, the condition under nitrogen gas or carbon dioxide gas atmosphere is preferable. More concretely, nitrogen gas, carbon dioxide gas, etc. are flowed through top surface in the fermenter with stirring and temperature of medium is adjusted to 33° C. When the temperature of the medium is stabilized at 33° C., propionic acid bacteria starter is inoculated to initiate the culture under anaerobic conditions. Activation culture liquid of propionic acid bacteria, microbial cell concentrate of the culture liquid can be used as the starter. Amount to be added in the medium is about 0.05% in the former case with respect to the medium and about 0.3% in the latter case only as a guide, however these amounts can be changed if necessary.

Culture can be performed under condition of culturing temperature at 20 to 40° C. and pH of the medium with neutral or weakly acidic, preferably at pH 5.5 to 7.5. For suppressing increase of acidity during the culture, known neutralizing agent such as aqueous potassium carbonate solution, aqueous sodium carbonate solution, etc. can be used.

A method for aerating to the medium will be explained hereinbelow. It is particularly surprising in view of the fact that amount of DHNA production is increased by such a means. Reasons for increase of the amount of DHNA production by continuous aeration have not been revealed; however, propionic acid bacteria initiates consumption of propionic acid by such an aeration.

Time for initiating aeration is when the concentration of carbon source in the medium reaches 3.5% by mass or less, and the time 24 hours before the carbon source for propionic acid bacteria has been used up can be used as a target for the initiation of the aeration. Time for initiating aeration is preferably at the time when concentration of the carbon source reaches 1.0 to 3.5% by mass, more preferably 1.5 to 3.0% by mass. Aeration at the time, when the concentration of carbon source reaches 3.5% by mass or less, makes the propionic acid bacteria to consume propionic acid in addition to the carbon source, and finally the carbon source will almost be used up. Numbers of propionic acid bacteria in the medium at the initiation of aeration are $1.0 \times 10^{10}$ cfu/ml (10.0 log cfu/ml) or more, preferably $1.4 \times 10^{10}$ cfu/ml (10.1 log cfu/ml) or more. By such an operation, carbon sources in the medium can be almost used up. In the medium containing lactose and under the culture condition described hereinabove, the concentration of lactose reaches 3.5% by mass or less at about 48 hours after initiating the culture, and it is the time for initiating the aeration. Although a culture method by which saccharide for carbon source such as lactose and glucose is added for propionic acid bacteria in the course of cultivation has been known (e.g. Patent document 1: JP-A-10-304871), such saccharides are preferably consumed in the present invention without adding in the course of culturing.

Amount of air to be supplied by aeration is preferably the amount sufficient to stimulate propionic acid bacteria. Specific example of such a condition corresponding to a laboratory scale (volume 1.5 lit.) is mentioned as follows. When the culture is performed under the condition using sparger with stirring propeller at 150 rpm, amount of supplied air is 2 lit. or more/min., preferably 2 lit./min. to 4 lit./min., and can be adjusted properly in conformity to the volume, stirring rate, apparatus, etc. When dissolved oxygen in the liquid becomes high beyond necessity, proliferation of propionic acid bacteria is terminated and production of DHNA is also terminated. In the case of the medium and the culture condition hereinbefore, the culture is generally terminated at about 168 hours from the initiation of the culture.

Aeration method includes a method for supplying air from whole surface of tube by inserting the porous aeration tube in the medium, or a method for supplying air bubble by using sparger.

The thus accumulated DHNA in the medium and microbial cells can be collected from the culture immediately after termination of the culture. Terminal point of the culture can be determined roughly on 3 to 5 days after numbers of microbial cells reaches the stationary phase and the carbon source in the medium has been used up.

The method for producing DHNA by adding carbon source for propionic acid bacteria to the culture after termination of the culture and preserving at 3 to 20° C. under weak alkaline conditions will be explained here in below. The culture herein can be the culture after performing the aeration herein before, but it may be the culture after termination of the culture under the condition of conventional anaerobic or slightly aerobic condition without aeration process.

Amount of carbon source to be added to the culture is preferably set to 0.2 to 3.0% by mass, preferably 0.4 to 2.5% by mass, more preferably 0.8 to 2.2% by mass of concentration of the carbon source in the culture. Further, weak alkaline condition can be maintained to pH 7 to 9, preferably pH 7.5 to 8.5 by adding base such as potassium carbonate, sodium carbonate and sodium phosphate. Preservation temperature is 3 to 20° C., preferably 3 to 15° C., more preferably 5 to 15° C. Preservation term is preferably 1 to 3 weeks, more preferably 1 to 2 weeks.

Content of DHNA in the culture can be improved by preservation at low temperature under such weak alkaline condition. The method of the present invention without necessitating new facilities, with small-space and with maintaining increased amount of DHNA during the preservation can be said as extremely useful and effective method for production.

A method for collecting DHNA will be explained hereinbelow. The obtained culture is preferably subjected to adsorption chromatography. Activated charcoal and reverse phase adsorbing agents such as synthetic adsorbing agent (e.g. Diaion HP-20, Mitsubishi Chemical Corp.) as examples of adsorbing agent can be used widely. Adsorbing agent is filled in a column and washed with aqueous sodium ascorbate 0.5% by weight solution. The obtained culture is added on a column (a liquid passed through the column is defined as "PASS") and the column is washed with aqueous sodium ascorbate 0.5% by weight solution to remove water soluble fraction. Thereafter, a solution of sodium ascorbate 0.5% by weight in ethanol is passed through the column for elution, and the eluted fraction of the ethanol solution is concentrated to obtain the composition containing high concentration of DHNA. Pure DHNA or salt thereof can be obtained by performing further purification. Methanol and other alcohol in place of ethanol can be used for eluting DHNA from the column. Further, as for the method replacing the above, isolation of DHNA can be performed by using liquid chromatography from the supernatant collected by centrifugation of the culture. Sodium erythorbate can be preferably used in place of sodium ascorbate. These compounds can be used as stabilizing agent for DHNA, and in the present invention, ascorbic acid, erythorbic acid, free acid thereof, fatty ester and other various esters, alkali metal salts, and other salts can also be used.

Examples of salt of DHNA are pharmaceutically or dietetically acceptable salts thereof, and representative salts include monovalent metal salt such as sodium, potassium, lithium, multivalent metal salt such as magnesium, calcium, zinc, and inorganic or organic amine salt such as ammonia and ethanolamine. Salt exchange can be performed by using known reaction. Examples of such salts are salt with inorganic acid (e.g. hydrochloric acid, phosphoric acid, hydrobromic acid and sulfuric acid), or salt with organic acid (e.g. formic acid, propionic acid, fumaric acid, maleic acid, succinic acid, tartaric acid, citric acid, malic acid, oxalic acid, benzoic acid, methanesulfonic acid and benzenesulfonic acid). These are illustrative only and the present invention is not limited to such salts.

Since DHNA is contained in the culture of DHNA producing bacteria (intra-microbial cells and/or extra-microbial cells), the culture itself can be concentrated by using rotary evaporator without applying adsorption chromatography to obtain the composition containing high concentration of DHNA. Separation of microbial cells from the culture by using conventional centrifugation and concentration of the obtained supernatant is preferable. The thus obtained composition can be used in the form of liquid state in conformity to a desired form for utilization or can be processed to powder state.

The thus obtained composition containing DHNA has high concentration of DHNA with suppressed bitter taste and good flavor. Consequently, the composition containing DHNA, or DHNA or salt thereof can be utilized in any forms of food and beverages or pharmaceuticals. For example, improvement of intestinal flora or reducing abdominal discomfort-observed in ingestion of milk, and prevention and treatment of metabolic osteopathy can be achieved by administering directly as the pharmaceuticals, or by directly ingesting food for special dietary use such as food for specified health use, or food with nutrient function claims, or by ingesting various foods (milk, refreshment, fermented milk, yoghurt, cheese, bread, biscuit, cracker, pizza, crust and others) added therewith.

In the production of foods described above, water, protein, saccharides, lipids, vitamins and minerals, organic acids, fruit juice, flavor, etc can be added in combination as a main component. For example, animal and plant proteins such as dry whole milk, skim milk, partially-skimmed milk, casein, whey powder, whey protein, whey protein concentrate, whey protein separate, α-casein, β-casein, β-lactoglobulin, α-lactalbumin, lactoferrin, soybean protein, egg protein, meat protein, etc., hydrolyzate thereof, various milk derived components such as butter, whey mineral, cream, whey, nonprotein nitrogen, sialic acid, phospholipids and lactose; carbohydrates such as sucrose, glucose, fructose, sugar alcohols, malt sugar, oligosaccharides, processed starch (dextrin, soluble starch, British starch, oxidized starch, starch ester, starch ether, etc.) and dietary fiber; animal oil and fat such as lard and fish oil; vegetable oil such as palm oil, safflower oil, corn oil, canola oil, copra oil, etc. and vegetable oil such as fractionated oil, hydrogenated oil, ester exchanged oil, etc.; various vitamins such as vitamin A, vitamin B group, vitamin C, erythorbic acid, vitamin D group, vitamin E, vitamin K group, vitamin P, vitamin Q, niacin, nicotinic acid, pantothenic acid, biotin, inositol, choline, folic acid, etc.; minerals such as calcium, potassium, magnesium, sodium, chlorine, copper, iron, manganese, zinc, selenium, fluorine, silicon, iodine, etc.; and organic acid such as malic acid, citric acid, lactic acid, tartaric acid and salt thereof can be mentioned, and one or two or more selected therefrom can be properly selected and added. Various components thereof can be preferably added in the form of synthetic products and if necessary in the form of foods containing large amounts thereof. The form thereof is not specifically limited to the aforementioned foods and is not limited if the final products maintain activity, and any forms such as liquid, solid (including granules, powder, tablets and gelled substance), semisolid substance (including jellied products), paste, emulsion, etc. can be used.

When the composition, or DHNA or salt thereof of the present invention is used as pharmaceuticals, it can be administered in various forms. Oral administration in the form of, for example, tablets, capsules, granules, powdered medicine, syrup, etc. can be mentioned. Such the pharmaceutical preparation can be formulated by using the main ingredient and the known auxiliary substances conventionally used in the pharmaceutical formulation technical field such as diluents, binders, disintegrators, lubricants, corrigents, solubilizing agents, suspensions, coating agents, etc.

EXAMPLES

The present invention will be explained hereinbelow by mentioning Test Examples and examples, but the present invention is not limited by them. In the Test Examples and examples hereinbelow, quantitative determination of DHNA was performed according to the method described in WO 03-016544, page 9. Measurement of concentration of lactose was performed by flow injection analysis using lactose electrode (Oji Scientific Instruments, Flow injection analyzer, Bio Flow Analyzer (Tradename)). The number of propionic acid bacteria was measured in a BL agar medium. Concentration of propionic acid and acetic acid were measured by HPLC (column: RS pak KC-811+precolum KC-G, detection: UV 445 nm).

Test Example 1

Examination on Various Aeration Initiation Times (1) Preparation of Medium

Skim milk (Meiji Dairies Corp.) 150 g was dissolved in 1000 g of water and the temperature of the solution was adjusted at 47° C. Protease 3.75 g was added thereto to hydrolyze protein at 47° C. for 6 hours. The pH of the reaction mixture during protein hydrolysis was adjusted to 6.6 to 6.8 by using aqueous potassium carbonate solution. After the hydrolysis of protein, the reaction mixture was maintained at 80° C. for 10 minutes to inactivate protease, supplied with beer yeast extract 7.5 g and adjusted at pH 6.95 using aqueous potassium carbonate solution. The volume of solution was adjusted to 1500 ml by adding water, and the solution was poured into a 2 lit. fermenter, and then the medium was sterilized. Sterilization condition was set at 121° C. for 7 minutes.

(2) Culture Condition

Nitrogen gas was ventilated through the fermenter, and the temperature of the medium was stabilized at 33° C., then the freeze concentration starter (*P. freudenreichii* ET-3) 0.75 ml was added to initiate culturing. Temperature during fermentation was adjusted at 33° C. and pH was adjusted to 6.5, and nitrogen gas was ventilated. Adjustment of pH was performed using 40% by weight aqueous potassium carbonate solution. A total of five culturing methods as described below was performed.

1) Continuing nitrogen gas ventilation from initiation till termination of culturing;
2) Same as in the above 1) except that lactose 2% by weight was added after 72 hours and 96 hours from initiation of culturing;
3) Nitrogen gas ventilation was switched to aeration (2 lit./min.) after 24 hours from initiation of culturing;
4) Ventilation was switched to the aeration (2 lit./min.) after 48 hours from initiation of culturing; and
5) Ventilation was switched to the aeration (2 lit./min.) after 72 hours from initiation of the culture.

These were all terminated after 168 hours from initiation of the culture.

(3) Results

Figure 2:
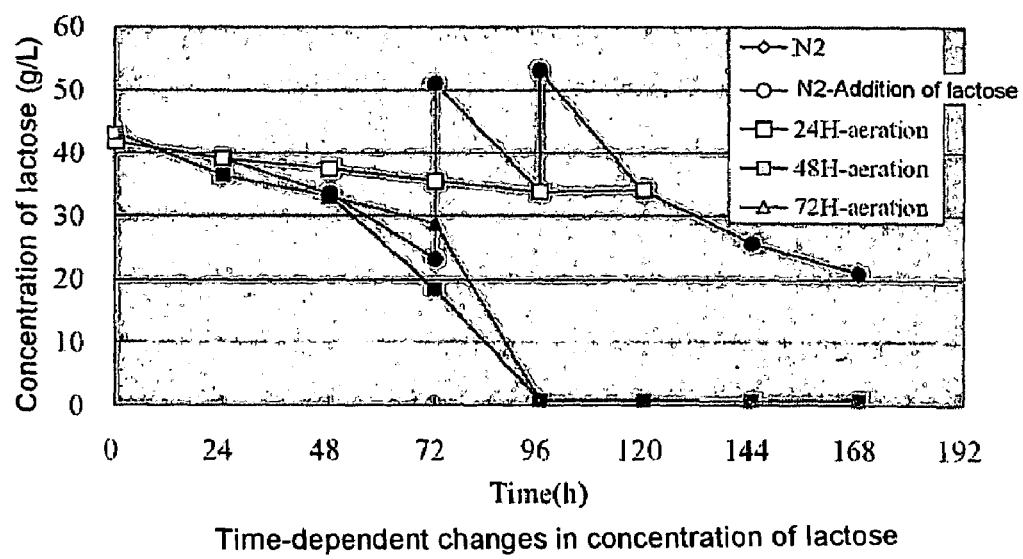
FIG. 2 shows changes in concentration of lactose due to varied initiation times of aeration.
Figure 3:
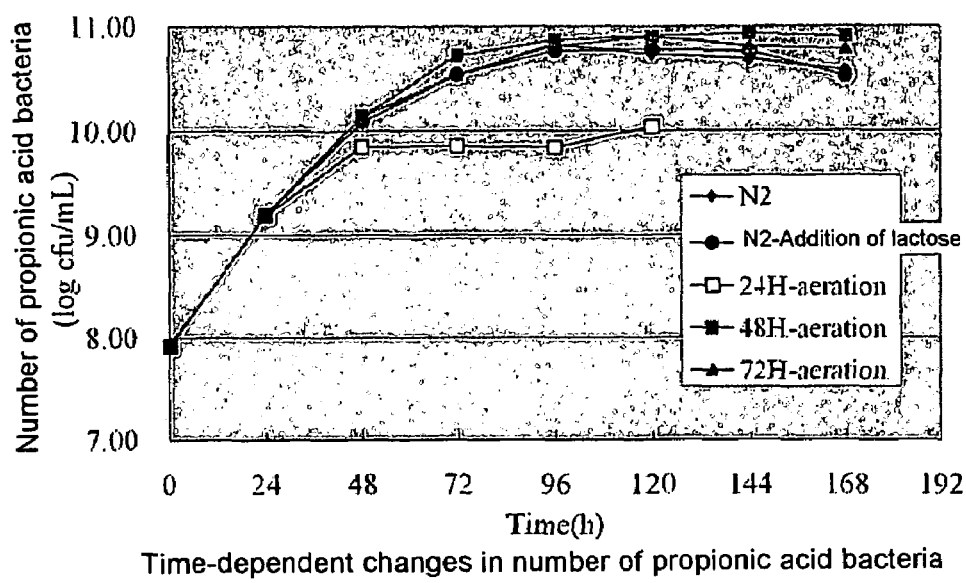
FIG. 3 shows relationship between the initiation time of aeration and number of propionic acid bacteria.
Figure 4:
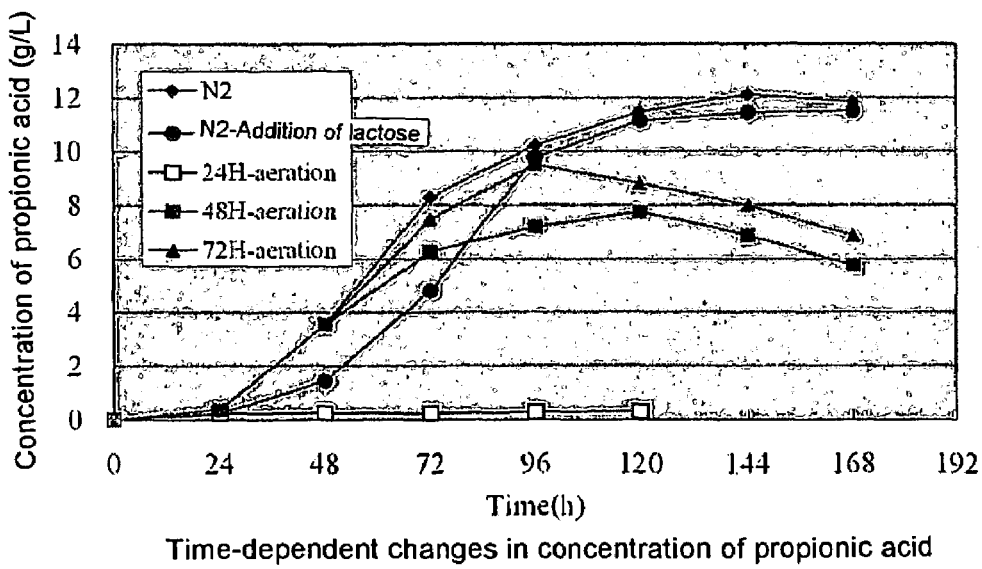
FIG. 4 shows concentration of propionic acid due to varied initiation times of aeration.
Figure 5:
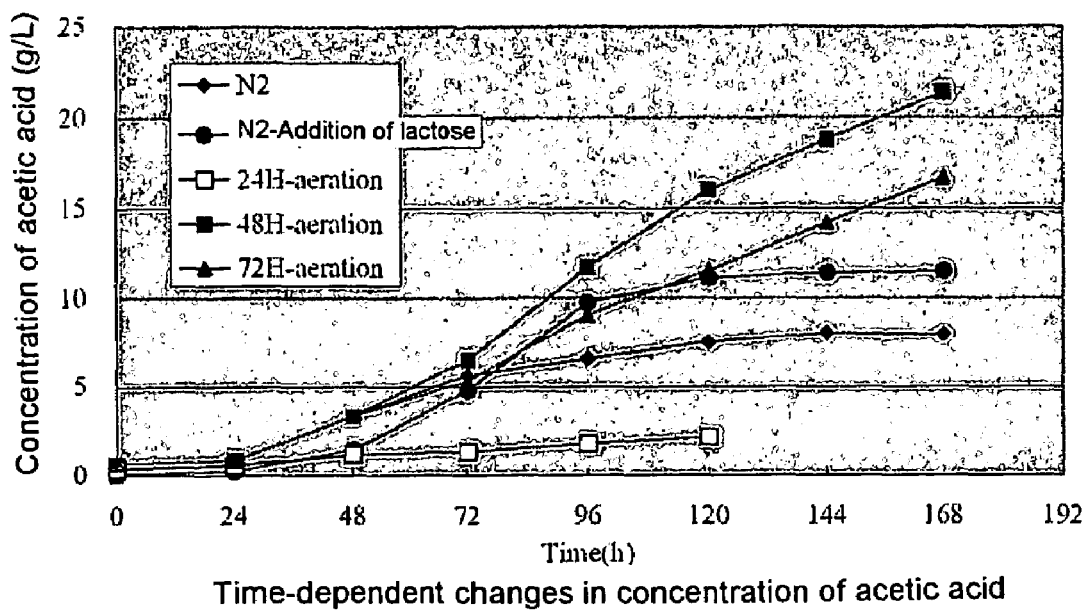
FIG. 5 shows concentration of acetic acid due to varied initiation times of aeration.

Changes in a time-dependent manner of concentration of DHNA, concentration of lactose, numbers of propionic acid bacteria, concentration of propionic acid, and concentration of acetic acid are shown in FIG. 1, FIG. 2, FIG. 3, FIG. 4 and FIG. 5, respectively. As obvious from the results, the culture obtained in 4) and 5) showed that the concentration of DHNA was about 45 µl/ml (FIG. 1). In 4) and 5), lactose was almost used up after 96 hours (FIG. 2), and a concentration of propionic acid which has been increased from initiation of the culture was confirmed to have gradually decreased (FIG. 4). Numbers of propionic acid bacteria exceeded in all the example culturing conditions except 3) to above $1.0 \times 10^{10}$ cfu/ml (10.0 log cfu/ml), and reached about $1.0 \times 10^{11}$ cfu/ml (11.0 log cfu/ml) in 4) and 5) (FIG. 3).

Figure 6:
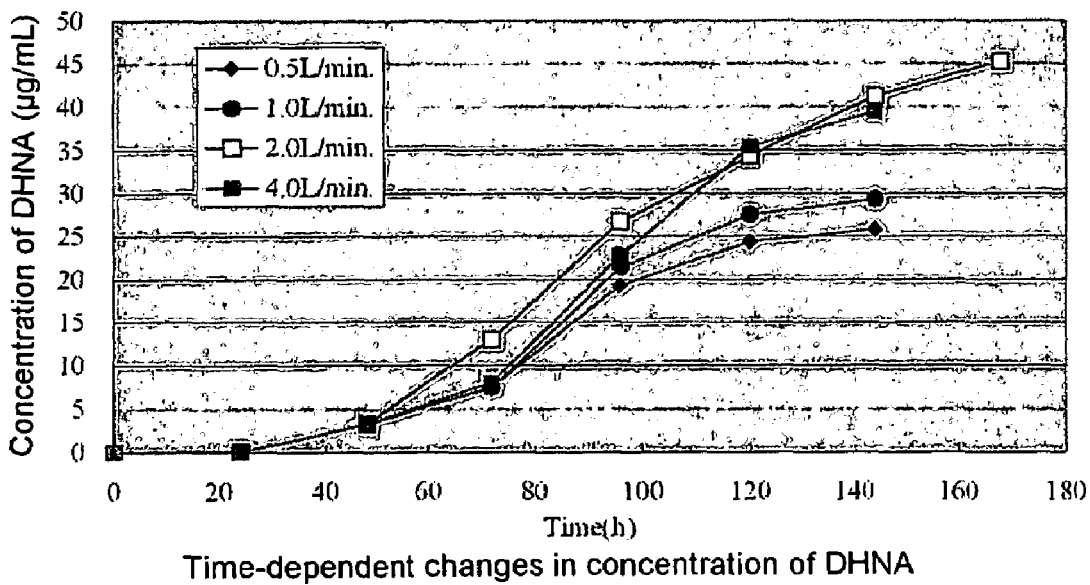
FIG. 6 shows concentration of DHNA due to varied initiation times of aeration.

From the above results, it was confirmed that the culture containing high concentration of DHNA could be obtained by switching from the nitrogen gas ventilation to aeration at least after 48 hours passing from initiation of the culture (FIG. 6). In addition, concentrations of lactose at the time of switching were 3.3% by mass in 4) and 2.9% by mass in 5) (FIG. 2).

Test Example 2

Examination on Aeration Volume

Culture was performed by the same condition as in Test Example 1, 5) except for changing the aeration volume. Aeration volume was changed to 0.5 lit./min., 1.0 lit./min., 2.0 lit./min. and 4.0 lit./min. after 72 hours from initiation of the fermentation. As a result, it was found that concentration of DHNA reached about 40 µg/ml after 144 hours from initiation of the culture by maintaining the flow rate at 2.0/min. or more.

Example 1

Skim milk (Meiji Dairies Corp.) 180 g was dissolved in water 1000 g and the solution was adjusted in temperature at 47° C. Protease 3.75 g was added thereto to hydrolyze protein at 47° C. for 3 hours. pH of the reaction mixture during protein hydrolysis was adjusted to pH 6.6 to 6.8 by using aqueous potassium carbonate solution. After the hydrolysis of protein, the reaction mixture was heated to 80° C. and maintained for 10 minutes to inactivate protease, supplied with beer yeast extract 7.5 g and lactose 15 g, and adjusted at pH 6.95 by using aqueous potassium carbonate solution. A volume of solution was adjusted to 1500 ml by adding water, the solution was poured into the 2 lit. volume fermenter, and the medium was sterilized (concentration of lactose about 6.1% by mass). Sterilization condition was set at 121° C. for 7 minutes. After the sterilization, nitrogen gas was ventilated through the fermenter, and temperature of the medium was stabilized at 33° C., then the freeze concentration starter (*P. freudenreichii* ET-3) 0.75 ml was added to initiate the culture. Temperature during fermentation was adjusted at 33° C. and pH was adjusted to pH 6.5, and nitrogen gas was ventilated. Adjustment of pH was performed using 40% by weight aqueous potassium carbonate solution. Ventilation of nitrogen gas was switched to the aeration after 72 hours from initiation of the culture, and the culture was terminated after 168 hours from initiation of the culture. Aeration rate of air at the aeration was set to 2 lit./min. and agitation rate was set to 150 rpm. As a result, the culture with concentration of DHNA 52 µg/ml could be obtained. Concentration of lactose after 72 hours was about 1.9% by mass and numbers of propionic acid bacteria were $3.5 \times 10^{10}$ cfu/ml.

Example 2

Skim milk (Meiji Dairies Corp.) 120 kg was dissolved in water 750 kg and the solution was adjusted in temperature at 47° C. Protease 2.5 kg was added thereto, and the mixture was adjusted to pH 7.6 to hydrolyze protein at 47° C. for 3 hours. After the hydrolysis was completed, the reaction mixture was heated to 80° C. and maintained for 10 minutes to inactivate protease, supplied with beer yeast extract 5 kg and lactose 10 kg, and the medium was sterilized at 140° C. for 4 seconds. pH of the medium before initiation of the sterilization was pH 6.9. After the sterilization, the volume of the medium was adjusted to 1000 lit. by adding water (concentration of lactose about 6.1% by mass), and nitrogen gas was ventilated at 20 lit./min. through the fermenter, and temperature of the medium was stabilized at 33° C., then the starter (*P. freudenreichii* ET-3) 3.0 lit. was added. Temperature during fermentation was adjusted at 33° C. and pH was adjusted to 6.5, and nitrogen gas was ventilated. Adjustment of pH was performed using 23% by weight aqueous potassium carbonate solution. Ventilation of nitrogen gas was switched to the aeration after 72 hours from initiation of the culture, and the culture was terminated after 168 hours from initiation of the culture. Air mass flow at the aeration was set to 200 lit./min. and agitation rate was set to 52 rpm. As a result, the culture with concentration of DHNA 42 µg/ml could be obtained. Concentration of lactose after 72 hours from initiation of the culture was about 1.5% by mass and numbers of propionic acid bacteria were $3.0 \times 10^{10}$ cfu/ml.

Example 3

To the culture containing DHNA obtained in example 2 hereinabove was added sodium ascorbate 1.0% and lactose 2.0%, and the pH of the mixture was adjusted to 8.0, and preserved at 10° C. for 2 weeks to obtain concentration of DHNA 55 µg/ml.

Lactose was replaced by glucose and the mixture was preserved in a same manner as above, and as a result, concentration of DHNA was increased compared to that at the time of termination of the culture.

Comparative Example

The culture was performed in the same condition as in example 1, except that aeration was not switched and nitrogen gas ventilation was continued during the culture. As a result, the culture with concentration of DHNA 32 µg/ml was obtained.

Example 4

Results of sensory evaluation of yoghurt prepared by adding the culture containing DHNA obtained in example 1 hereinbefore to plane yoghurt 120 g (Meiji Dairies Corp.) are shown in Table 1 and Table 2. It was confirmed that the yoghurt with the added culture containing DHNA obtained by the method of the present invention had high concentration of DHNA, and had neither acid taste nor bitter taste as compared with yoghurt prepared by the conventional method (i.e. to the plane yoghurt was added the culture containing DHNA obtained by Comparative Example).

TABLE 1

| Item | Flavor | Acid taste | Bitter taste | Overall judgment |
| --- | --- | --- | --- | --- |
| Culture prepared in Example 1 | Good | Good | None | Very Good |
| Culture prepared in Comparative Example | Good | Good | Bad | Fair |

1 g added to plane yoghurt
Plane yoghurt: 120 g

TABLE 2

| Item | Flavor | Acid taste | Bitter taste | Overall judgment |
| --- | --- | --- | --- | --- |
| Culture prepared in Example 1 | Fair | Good | None | Good |
| Culture prepared in Comparative Example | Fair | Fair | Bad | Bad |

2 g added to plane yoghurt
Plane yoghurt: 120 g

Example 5

Skim milk (Meiji Dairies Corp.) 120 kg was dissolved in water 750 kg and the solution was adjusted in temperature at 47° C. Protease 2.5 kg was added thereto, pH of the solution was adjusted to pH 7.6 to hydrolyze protein at 47° C. for 6 hours. After the hydrolysis was completed, the reaction mixture was heated to 80° C. and maintained for 10 minutes to inactivate protease, supplied with beer yeast extract 5 kg and lactose 10 kg, and the medium was sterilized at 140° C. for 4 seconds. pH of the medium before initiation of the sterilization was 6.9. After the sterilization, a volume of the medium was adjusted to 1000 lit. by adding water (concentration of lactose about 6.1% by mass), and nitrogen gas was ventilated at 20 lit./min. through the fermenter, and temperature of medium was stabilized at 33° C., then the starter (*P. freudenreichii* ET-3) 3.0 lit. was added. Temperature during fermentation was adjusted at 33° C. and pH was adjusted to pH 6.5, and nitrogen gas was ventilated. Adjustment of pH was performed using 23% by weight aqueous potassium carbonate solution. Ventilation of nitrogen gas was switched to the aeration after 72 hours from initiation of the culture, and the culture was terminated after 168 hours from initiation of the culture. Air mass flow at the aeration was set to 200 lit./min. and agitation rate was set to 52 rpm. As a result, the culture with concentration of DHNA 48 µg/ml could be obtained. Concentration of lactose after 72 hours from initiation of the culture was about 3.0% by mass and numbers of propionic acid bacteria were $2.9 \times 10^{10}$ cfu/ml.

Example 6

To the culture containing DHNA obtained in example 5 hereinabove was added sodium ascorbate 1.0% and lactose 1.0%, the mixture was adjusted in pH to 8.0 and preserved at 10° C. for 2 weeks to obtain concentration of DHNA 60 µg/ml.

The invention claimed is:
1. A process for producing 1,4-dihydroxy-2-naphthoic acid comprising initiating a culture of 1,4-dihydroxy-2-naphthoic acid producing bacteria belonging to propionic acid bacteria under anaerobic conditions and culturing the bacteria under aeration into a medium wherein the concentration of a carbon source in the medium is 3.5% by mass or less.

2. The process according to claim 1, wherein the medium comprises 4 to 8% by mass of the carbon source.

3. The process according to claim 1 or 2, wherein the anaerobic conditions are conditions under nitrogen gas or carbon dioxide gas atmosphere.

4. A process for producing 1,4-dihydroxy-2-naphthoic acid, comprising initiating a culture of 1,4-dihydroxy-2-naphthoic acid producing bacteria belonging to propionic acid bacteria under anaerobic conditions, culturing the bacteria under aeration into a medium wherein the concentration of a carbon source in the medium is 3.5% by mass or less, adding the carbon source to the obtained culture and preserving the culture at 3 to 20° C. under weak alkaline conditions.

5. The process according to claim 4, wherein the medium comprises 4 to 8% by mass of the carbon source.

6. The process according to claim 4 or 5, wherein the anaerobic conditions are conditions under nitrogen gas or carbon dioxide gas atmosphere.

7. The process according to claim 4, wherein the amount of carbon source added to the culture is such that a concentration of the carbon source in the culture is 0.2 to 3% by mass.

8. The process according to claim 4, wherein the culture is preserved at pH 7 to 9 at 3 to 20° C. for 1 to 3 weeks.

9. The process according to claim 5, wherein the amount of carbon source added to the culture is such that a concentration of the carbon source in the culture is 0.2 to 3% by mass.

10. The process according to claim 6, wherein the amount of carbon source added to the culture is such that a concentration of the carbon source in the culture is 0.2 to 3% by mass.

11. The process according to claim 5, wherein the culture is preserved at pH 7 to 9 at 3 to 20° C. for 1 to 3 weeks.

12. The process according to claim 6, wherein the culture is preserved at pH 7 to 9 at 3 to 20° C. for 1 to 3 weeks.

* * * * *